(12) United States Patent
Luque Vera et al.

(10) Patent No.: US 11,351,562 B2
(45) Date of Patent: Jun. 7, 2022

(54) DEVICE AND METHOD FOR THE AUTOMATED DIFFUSION OF VOLATILE SUBSTANCES COMPRISING A PHOTOVOLTAIC CELL

(71) Applicant: ZOBELE HOLDING SPA, Trento (IT)

(72) Inventors: Sergio Luque Vera, Barcelona (ES); Dominic Doyle, Barcelona (ES); Chao Hsu Lee, Singapore (SG)

(73) Assignee: ZOBELE HOLDING SPA

( * ) Notice: Subject to any disclaimer, the term of this patent is extended or adjusted under 35 U.S.C. 154(b) by 0 days.

(21) Appl. No.: 16/065,845

(22) PCT Filed: Dec. 19, 2016

(86) PCT No.: PCT/EP2016/081721
§ 371 (c)(1),
(2) Date: Jun. 25, 2018

(87) PCT Pub. No.: WO2017/108677
PCT Pub. Date: Jun. 29, 2017

(65) Prior Publication Data
US 2019/0009294 A1    Jan. 10, 2019

(30) Foreign Application Priority Data

Dec. 23, 2015    (ES) ................. ES201531889

(51) Int. Cl.
*B05B 12/02*    (2006.01)
*A61L 9/14*    (2006.01)
(Continued)

(52) U.S. Cl.
CPC .............. *B05B 12/02* (2013.01); *A61L 9/127* (2013.01); *A61L 9/14* (2013.01); *H02S 40/38* (2014.12);
(Continued)

(58) Field of Classification Search
CPC ..... B05B 12/06; B05B 12/02; B05B 17/0646; B05B 17/0607; H02S 40/35; H02S 99/00;
(Continued)

(56) References Cited

U.S. PATENT DOCUMENTS 3,543,122 A * 11/1970 Klebanoff ................. H02P 7/03
318/443
3,589,563 A * 6/1971 Carragan ............. B65D 83/262
239/70
(Continued)

FOREIGN PATENT DOCUMENTS

CA          3009562       12/2016
EP      2 376 130 A1      10/2011
(Continued)

OTHER PUBLICATIONS

Spanish Search Report dated Nov. 30, 2016 (5 pages).
(Continued)

*Primary Examiner* — Joseph A Greenlund
(74) *Attorney, Agent, or Firm* — Ostrolenk Faber LLP (57) ABSTRACT

A device and method for diffusing volatile substances which obtains the energy required for the autonomous operation thereof from one or more photovoltaic cells. The activation periods and switch-on frequency of the emission means are determined adaptively by an electronic controller depending on the light conditions, thereby maximizing the time in which the device diffuses the volatile substance without compromising its autonomy.

11 Claims, 5 Drawing Sheets

(51) Int. Cl.
| | |
|---|---|
| *B65D 83/26* | (2006.01) |
| *A61L 9/12* | (2006.01) |
| *H02S 40/38* | (2014.01) |
| *H02S 99/00* | (2014.01) |

(52) U.S. Cl.
CPC ........... *H02S 99/00* (2013.01); *A61L 2209/11* (2013.01); *A61L 2209/132* (2013.01); *B65D 83/26* (2013.01)

(58) Field of Classification Search
CPC ........ A61L 9/127; A61L 9/14; A61L 2209/11; A61L 2209/132; B65D 83/26; A01M 1/205
USPC ............................................ 239/102.1, 102.2
See application file for complete search history.

(56) References Cited

U.S. PATENT DOCUMENTS

| | | | |
|---|---|---|---|
| 4,625,342 A | 12/1986 | Gangnath et al. | |
| 5,230,837 A * | 7/1993 | Babasade | F24F 3/12 |
| | | | 261/DIG. 65 |
| 5,675,845 A | 10/1997 | Martin et al. | |
| 5,884,808 A * | 3/1999 | Muderlak | B65D 83/262 |
| | | | 222/25 |
| 5,908,140 A * | 6/1999 | Muderlak | B65D 83/262 |
| | | | 222/646 |
| 6,182,904 B1 * | 2/2001 | Ulczynski | B05B 1/3053 |
| | | | 239/69 |
| 6,296,196 B1 * | 10/2001 | Denen | A01M 1/205 |
| | | | 239/102.1 |
| 6,347,414 B2 | 2/2002 | Contadini et al. | |
| 6,644,507 B2 | 11/2003 | Borut et al. | |
| 6,802,460 B2 * | 10/2004 | Hess | B05B 17/0676 |
| | | | 239/338 |
| 8,371,474 B2 * | 2/2013 | Tramontina | B05B 11/3097 |
| | | | 222/642 |
| 8,881,945 B2 * | 11/2014 | Gasper | A61L 9/125 |
| | | | 222/639 |
| 10,040,660 B1 * | 8/2018 | Malesky | H02P 29/00 |
| 10,264,781 B2 * | 4/2019 | Ryan | B05B 1/00 |
| 2001/0042794 A1 * | 11/2001 | Tomkins | B05B 17/0684 |
| | | | 239/102.2 |
| 2003/0168524 A1 | 9/2003 | Hess et al. | |
| 2005/0163670 A1 | 7/2005 | Alleyne et al. | ............... 422/125 |
| 2006/0011739 A1 | 1/2006 | Jaworski | |
| 2006/0115386 A1 * | 6/2006 | Michaels | A61L 9/14 |
| | | | 422/123 |
| 2006/0120080 A1 * | 6/2006 | Sipinski | H05B 45/44 |
| | | | 362/253 |
| 2006/0188238 A1 * | 8/2006 | Kent | B60H 3/0007 |
| | | | 392/394 |
| 2006/0261188 A1 * | 11/2006 | Ito | A01M 1/2044 |
| | | | 43/132.1 |
| 2007/0159422 A1 * | 7/2007 | Blandino | A61L 9/03 |
| | | | 345/82 |
| 2007/0204388 A1 | 9/2007 | Zyskowski et al. | ........... 4/228.1 |
| 2008/0027586 A1 * | 1/2008 | Hern | G01K 13/00 |
| | | | 340/602 |
| 2008/0073443 A1 * | 3/2008 | Tollens | B05B 17/0646 |
| | | | 222/638 |
| 2008/0127940 A1 * | 6/2008 | Stephan | F02M 53/06 |
| | | | 123/549 |
| 2008/0178518 A1 * | 7/2008 | Reece | A61L 9/122 |
| | | | 43/127 |
| 2010/0059602 A1 * | 3/2010 | Chiou | A01M 1/2038 |
| | | | 239/70 |
| 2010/0224697 A1 * | 9/2010 | Modlin | B05B 17/0684 |
| | | | 43/132.1 |
| 2011/0073151 A1 * | 3/2011 | Yago | H01L 31/0465 |
| | | | 136/244 |
| 2011/0259973 A1 * | 10/2011 | Pedicano | A61L 9/14 |
| | | | 239/44 |
| 2011/0290908 A1 * | 12/2011 | Tranzeat | A01M 1/2033 |
| | | | 239/44 |
| 2012/0222935 A1 * | 9/2012 | MacKay | G07F 17/248 |
| | | | 361/679.01 |
| 2014/0253336 A1 * | 9/2014 | Ophardt | C12Q 1/04 |
| | | | 340/573.1 |
| 2015/0008865 A1 * | 1/2015 | Wang | H05B 45/60 |
| | | | 315/308 |
| 2015/0313422 A1 * | 11/2015 | Ophardt | H01L 31/042 |
| | | | 222/1 |
| 2016/0030620 A1 * | 2/2016 | Peterson | A61L 9/042 |
| | | | 261/84 |
| 2016/0211799 A1 * | 7/2016 | Blick | H02S 40/38 |
| 2019/0009294 A1 * | 1/2019 | Luque Vera | H02S 99/00 |

FOREIGN PATENT DOCUMENTS

| | | |
|---|---|---|
| EP | 2376130 | 10/2011 |
| ES | 2619153 | 6/2017 |
| FR | 2864974 | 7/2005 |
| JP | 09-144101 | 3/1997 |
| JP | 2004233093 | 8/2004 |
| JP | 2005036511 | 10/2005 |
| WO | WO 2006/084317 A1 | 8/2006 |
| WO | WO 2010/070576 A1 | 6/2010 |

OTHER PUBLICATIONS

PCT Search Report dated Apr. 18, 2006 (4 pages).
International Search Report dated Mar. 20, 2017 in corresponding PCT International Application No. PCT/EP2016/081721.
Written Opinion dated Mar. 20, 2017 in corresponding PCT International Application No. PCT/EP2016/081721.

* cited by examiner

DEVICE AND METHOD FOR THE AUTOMATED DIFFUSION OF VOLATILE SUBSTANCES COMPRISING A PHOTOVOLTAIC CELL

CROSS-REFERENCE TO RELATED APPLICATIONS

The present application is a 35 U.S.C. §§ 371 national phase conversion of PCT/EP2016/081721, filed Dec. 19, 2016, which claims priority to Spanish Patent Application No. P201531889, filed Dec. 23, 2015, the entire contents of both applications being incorporated herein by reference. The PCT International Application was published in the English language.

OBJECT OF THE INVENTION

The present invention relates to the field of the automated dispensing of volatile substances, and more specifically to an autonomous solar energy-based device and method.

BACKGROUND OF THE INVENTION

There are various scenarios which require the periodic and automated emission of volatile substances, such as, insecticides or air fresheners, for example. Said substances are typically stored in a container in the form of liquids, gels, waxes, impregnated solids, etc. The substances can be released in a passive manner either by means of active elements such as fans, heaters, sprays, nebulizers, or aerosols. Active elements of this type allow both increasing diffusion efficiency, for example by means of generating an air stream which induces the diffusion thereof, and increasing the degree of control over said diffusion, which allows controlling substance emission intensity or temporarily programming substance release.

However, all the existing technologies have limitations in terms of energy consumption and/or adaptability to environmental conditions. For example, heaters have such a high energy consumption that they typically require connection to the electrical network. In turn, sprays, nebulizers and fans require a somewhat lower consumption, allowing the use of batteries, but they have to be replaced periodically. Furthermore, they can only be configured manually, not showing any capacity to adapt to changing environmental conditions.

For example, US 2005/0163670 A1 discloses a heat-activated car air freshener having a plug suitable for being connected to the cigarette lighter socket of an automobile. The air freshener comprises a fan generating an air stream picking up the volatile substance through a structure consisting of chambers and filters, and releasing it into the environment. In turn, US 2007/0204388 A1 discloses an air freshener system for bathrooms that is automatically coordinated with the use of a toilet tank. In this case, the device in charge of releasing the air freshener is powered from a battery that must be changed or charged periodically. These examples therefore have the same energy limitations described above.

Ultimately, there is still a need in the state of the art for an autonomous method and device for diffusing volatile substances which prevents the need for current sockets or replaceable batteries, and is capable of adapting to the environmental operating conditions in an automated manner.

DESCRIPTION OF THE INVENTION

The present invention solves the problems described above by means of an automated dispensing of volatile substances that is powered by light energy and adaptively modifies the emission of said substance depending on the light conditions existing at that time.

A first aspect of the invention relates to a device for the automated diffusion of one or more volatile substances comprising:

Emission means periodically diffusing the volatile substance. Said volatile substance is typically stored in a reserve container in solid or liquid state, the container being able to be integrated in the device or implemented in interchangeable vessels that can be connected to said device.

At least one photovoltaic cell which captures light energy present around the device and transforms it into electric energy that can be used by the emission means and by the other electronic elements of the device. It must be noted that the photovoltaic cell can be configured both to operate by means of transforming sunlight and by means of transforming artificial light. Likewise, the photovoltaic cell can be implemented according to any of the generic alternatives known in the state of the art for carrying out said energy transformation.

At least one battery which powers the emission means and stores the electric energy generated by the photovoltaic cell. The battery can be implemented, for example, by means of a capacitor, a supercapacitor or any other energy storage technology known in the state of the art.

An electronic controller determining activation intervals of the emission means depending at least on the amount of transformed light energy, thereby adapting to the light conditions present around the device. Preferably, the electronic controller is also based on the battery energy level for determining said intervals, thereby minimizing the time between activation intervals. Preferably, the electronic controller does not only determine the activation intervals, but also adapts the emission frequency of the emission means within each interval depending on the light conditions and/or on the battery energy level. By reducing the emission frequency when the energy reserves drop, the time in which the emission means are active is maximized.

With respect to the emission means, a series of preferred options are shown below. It must be noted, however, that said emission means can be implemented with any other technology for the automated diffusion of volatile substances known in the state of the art, provided that said technology can be controlled from an electronic controller:

A magnetically controlled movable body, the activation of which generates an airflow over a passive evaporation surface, allowing the diffusion of the volatile substance into the environment. The movable body comprises a magnet which allows controlling the same through magnetic flux generating means which in turn are controlled from the electronic controller.

An aerosol storing the volatile substance under pressure. The aerosol in turn comprises a valve that can be controlled from the electronic controller, for example, by means of an electrovalve or by means of a mechanical valve controlled by a rotary motor.

A piezoelectric mechanism controlled from the electronic controller. According to preferred options of the invention, the piezoelectric mechanism can be in direct contact with the volatile substance to be diffused or auxiliary elements such as a porous wick can be used.

A second aspect of the invention relates to a method for the automated diffusion of volatile substances which comprises the following steps:

Storing the electric energy obtained by means of photovoltaic transformation in a battery.

Adaptively determining emission intervals of the volatile substance and, preferably, an emission frequency within said intervals. For said adaptive determination, the method is based on the transformation of light energy into electric energy and, preferably, on the battery energy levels.

Extracting the electric energy stored in the battery.

Diffusing the volatile substance according to the predetermined intervals and frequencies, and using the extracted electric energy. An autonomous method which prevents the need for electrical connections or battery replacements and allows adapting to the environmental conditions in which it is run is thereby achieved.

It must be noted that any preferred option or particular embodiment of the device of the invention can be implemented in particular embodiments of the method of the invention, and vice versa.

Finally, a third aspect of the invention relates to a computer program comprising computer program coding means suitable for implementing the described method by running it in a computer, a digital signal processor, an application-specific integrated circuit, a microprocessor, a microcontroller or any other form of programmable hardware.

The device, method, and computer program that have been described therefore provide autonomous diffusion preventing the need for electrical connections or battery replacements. Likewise, it is capable of adapting to changing light conditions, optimizing the emission of the volatile substance without compromising the device in terms of energy. The foregoing and other advantages of the invention will be apparent in view of the detailed description thereof.

DESCRIPTION OF THE DRAWINGS

For the purpose of aiding to better understand the features of the invention according to a preferred practical embodiment thereof, and for complementing this description, the following illustrative and non-limiting drawings are attached as an integral part thereof:

FIG. 5 schematically shows in greater detail the elements forming the emission means according to a preferred embodiment of the device based on

PREFERRED EMBODIMENT OF THE INVENTION

In this text, the words "comprises" and its variants (such as "comprising", etc.) must not be understood in an excluding manner, i.e., these terms must not be interpreted as excluding the possibility that what is described and defined may include more elements, steps, etc.

Figure 1:
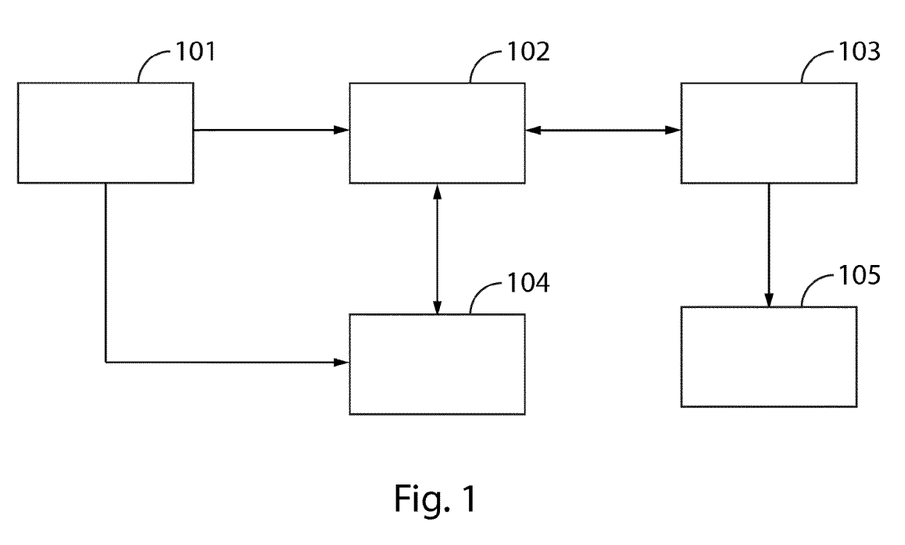
FIG. 1 schematically shows the main elements making up a preferred embodiment of the device of the invention.

FIG. 1 schematically shows the main elements of a preferred embodiment of the device of the invention which in turn implement a preferred embodiment of the method of the invention. The device comprises one or more photovoltaic cells (101) powering an electronic controller (102) and emission means (103) directly and through a battery (104) storing the electric energy generated by the photovoltaic cell (101). The device can further comprise one or more containers (105) in which the volatile substances to be diffused are stored. Said substances can be stored in the form of liquids, gels, waxes, impregnated solids, or any other form known in the state of the art. Likewise, the containers (105) can either be integrated in the device, or they can be interchangeable independent elements. If they are independent elements, the device comprises the fixing elements required to allow the fixing of said containers (105) and the actuation of the emission means (103) thereon.

The photovoltaic cell (101) makes the device autonomous by supplying the electric energy required for the operation of the electronic controller (102), the emission means (103), as well as any other additional element integrated in the device. Likewise, it provides the electronic controller (102) with information concerning the environmental light conditions through the amount of light energy transformed into electric energy in said photovoltaic cell (101), allowing adaptive control of the emission means (103). The electronic controller (102) can be implemented, for example, in an application-specific integrated circuit, a microprocessor, a microcontroller or any other form of programmable hardware, said electronic controller (102) comprising computer program coding means which implement the adaptive control of the emission means (103) when being run.

Figure 2:
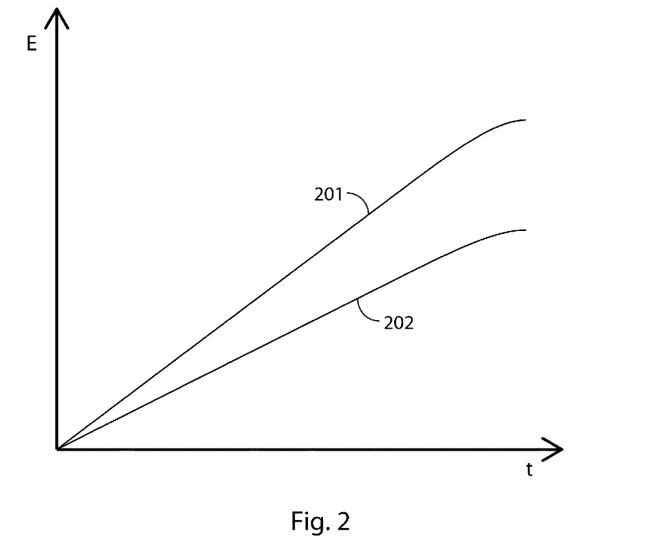
FIG. 2 shows by way of example the process of capturing light energy in two different light conditions performed by preferred embodiments of the device and method of the invention.

FIG. 2 shows the electric energy (E) generated over time (t) for first environmental conditions (201) and second environmental conditions (202). Since there is more light in the first environmental conditions (201), the speed at which electric energy is generated is also greater, a steeper slope being observed. Said slope is measured by the electronic controller (102) and used for adaptively modifying the control of the emission means (103). Additionally or alternatively, the electronic controller (102) can use the battery energy level (103) as input information for performing adaptive control since said level is directly related to the amount of transformed light energy. The adaptive control performed by the electronic controller (102) determines the time intervals in which the emission means (103) are active, i.e., the time intervals in which the emission means (103) are actively causing the diffusion of the volatile substance. For simplicity, said time intervals are referred to as active intervals ($t_{ON}$), and the intervals in which the emission means (103) are not causing the diffusion of the volatile substance are referred to as inactive intervals ($t_{OFF}$). It must be noted that during an active interval ($t_{ON}$), the action of the emission means (103) is not continuous, rather they have a periodic behavior with frequency that can be controlled. Likewise, during an inactive interval ($t_{OFF}$), the volatile substance in some particular embodiments of the device of the invention can present passive diffusion such as evaporation, for example, said passive diffusion always being smaller than the diffusion obtained when actuating the emission means (103).

Figure 3:
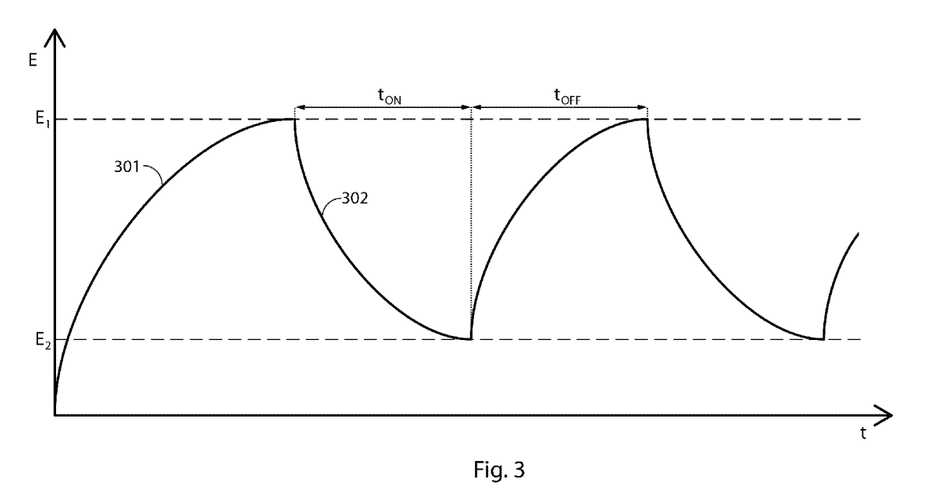
FIG. 3 illustrates the energy charging and discharging cycles, corresponding to the switch-on and switch-off intervals of the emission means, according to preferred embodiments of the device and method of the invention.

FIG. 3 shows in greater detail the succession of active intervals ($t_{ON}$) and inactive intervals ($t_{OFF}$), determined depending on the amount of transformed light energy in the photovoltaic cell (101). In particular, the electronic controller (102) determines the active intervals ($t_{ON}$) and inactive intervals ($t_{OFF}$) depending on the level of energy (E) in the battery (104), in turn defined by said light energy transformation and device consumption. During the inactive intervals ($t_{OFF}$), the emission means (103) are switched off, the charging (301) of the battery (104) being generated. During the active intervals ($t_{ON}$), the consumption of the emission means is greater than the electric energy provided by the photovoltaic cell (101), the discharging (302) of the battery occurs.

In particular, a preferred embodiment of the method of the invention implemented in a preferred embodiment of the electronic controller (102) of the invention establishes two thresholds of energy stored in the battery (104) for adaptively determining the active intervals ($t_{ON}$) and inactive intervals ($t_{OFF}$). When a first level ($E_1$) is reached, the electronic controller (102) activates the emission means (103) and an active interval ($t_{ON}$) starts. Then, when the energy stored in the battery (104) drops to a second level ($E_2$), lower than the first level ($E_1$), the electronic controller (102) stops the emission means (103), starting an inactive interval ($t_{OFF}$).

Within each active interval ($t_{ON}$), the emission frequency of the emission means (103) is adaptively controlled by the electronic controller (102) depending on the light conditions measured through the energy generated by the photovoltaic cell (101). It must be noted that emission frequency is understood as the frequency at which the emission means (103) act on the volatile substance, inducing its diffusion, said actuation being variable in nature according to the particular embodiment of said emission means (103). For example, said emission frequency can be the frequency with which an air stream over the volatile substance is generated, the frequency with which a magnetic or piezoelectric element is moved or, etc.

Figure 4:
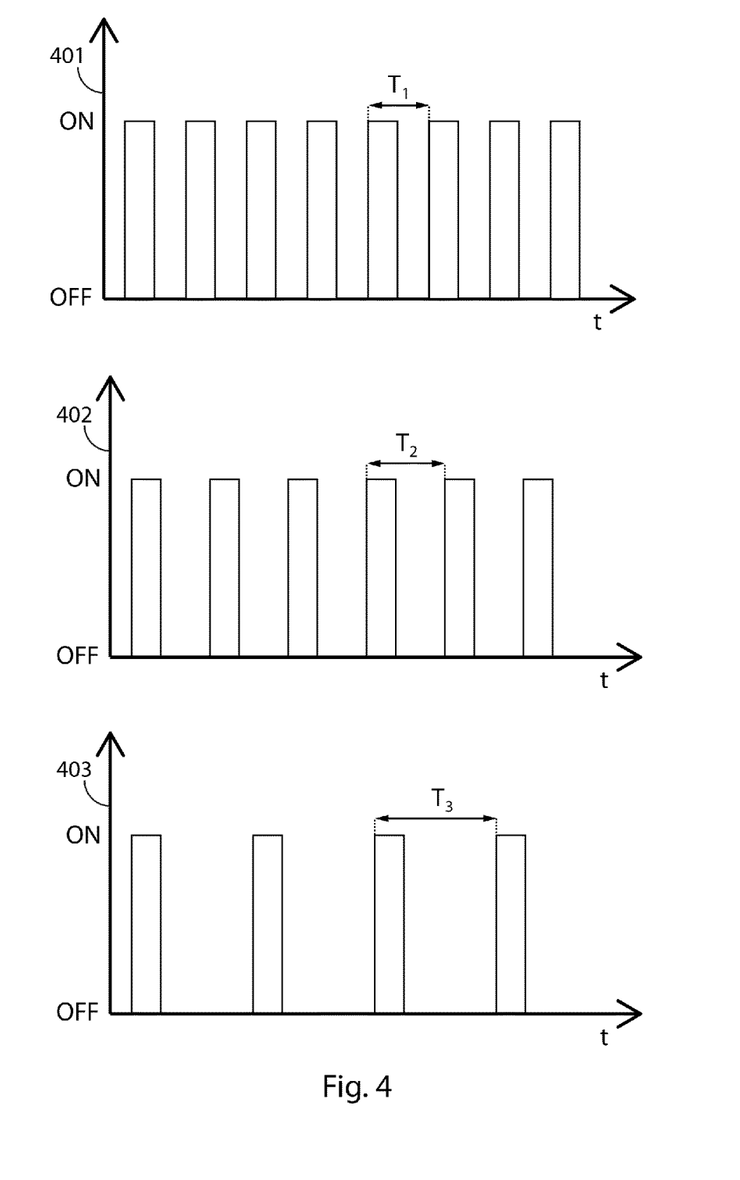
FIG. 4 shows the change in the emission frequency depending on the light conditions performed by preferred embodiments of the device and method of the invention.

FIG. 4 shows by way of example the adaptive control of the emission frequency within the active intervals ($t_{ON}$). In other words, within each active interval ($t_{ON}$) there are instants in which diffusion (ON) occurs and instants in which diffusion (OFF) does not occur. Said instants alternate in a periodic manner, with a variable period that can be controlled by the electronic controller. FIG. 4 shows a first interval (401) in which there is a high electric energy supply by the photovoltaic cell (101), so a first period ($T_1$) generating a high volatile substance emission is determined. In a second interval (402) in which the electric energy supplied by the photovoltaic cell (101) decreases, it increases to a second period ($T_2$) in order to reduce electric consumption and increase the duration of the battery (104). Finally, in a third interval (403) in which the energy supplied is even less, the emission is further reduced by means of a third period ($T_3$).

The adaptive determination of the active intervals ($t_{ON}$) and their emission frequency is therefore configured for maximizing the duration of the active intervals ($t_{ON}$) and the autonomy of the battery (104). It must be noted, however, that various modifications can be made on the described adaptive determination algorithm within the object of the invention as claimed, provided that the diffusion of the volatile substance is reduced as the amount of light received in the photovoltaic cell (101) decreases. For example, maximum and minimum limits can be established for the different control parameters of the emission means (103), the emission intensity (103) and the frequency can be acted on, a variable frequency can be used within one and the same active interval ($t_{ON}$), additional input parameters can be used for determining the active intervals ($t_{ON}$) and their emission frequency that are fixed or can be controlled by a user, etc.

Figure 5:
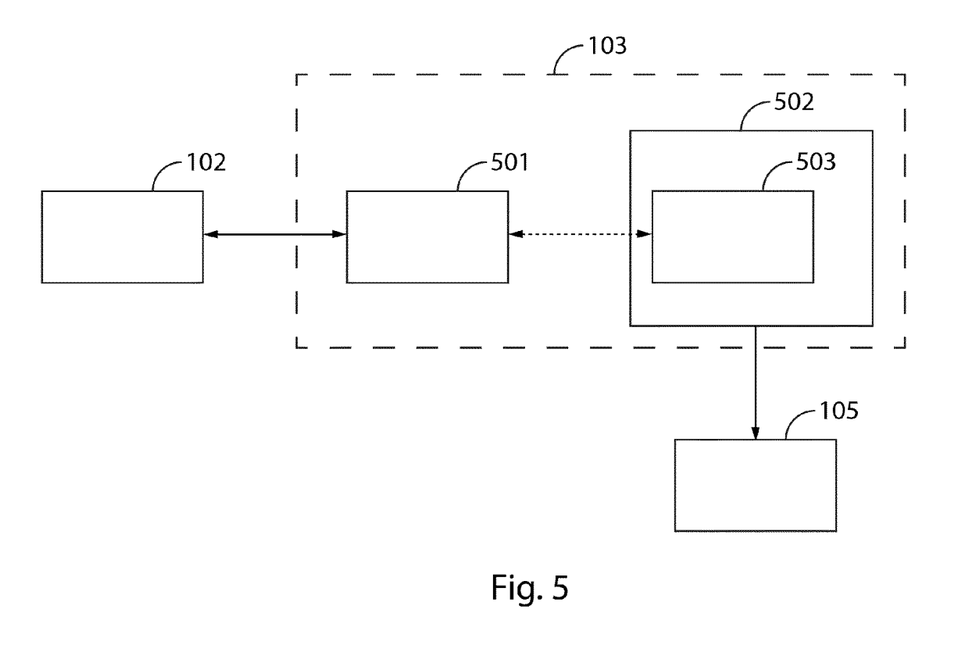

Finally, FIG. 5 schematically shows the particular case in which the emission means (103) is implemented by means of magnetic elements. In particular, the emission means (103) comprise a movable element (502), the movement of which generates an airflow over a passive surface. Preferably, the container (105) is attached to the movable element (502), a container (105) being able to be replaced. The movable element (502) in turn comprises a magnet (503), the movement of which is activated by means of magnetic flux generating means (501), such as an induction coil with variable input current. The magnetic flux generating means (501) are in turn controlled from the electronic controller (102) for establishing the desired oscillation frequency on the magnet (503), and therefore defining the emission frequency depending on the light conditions which optimizes system performance. By changing the activation frequency of the emission means (103), the speed thereof and therefore, airflow generation also changes.

In view of this description and drawings, the person skilled in the art will be able to understand that the invention has been described according to some preferred embodiments thereof, but that a number of variations can be introduced in said preferred embodiments without departing from the object of the invention as claimed. In particular, it must be noted that the emission means (103) based on controlling by means of magnetic flux can be replaced with any other technology for the diffusion of volatile substances known in the state of the art, provided that said technology allows the adaptive control thereof from an electronic controller (102).

The invention claimed is:

1. A device for automated diffusion of at least one volatile substance, the device comprising:
    a volatile substance emitter configured to diffuse the at least one volatile substance;
    at least one battery;
    at least one photovoltaic cell configured to transform light energy into electric energy and to store said electric energy in the at least one battery; and
    an electronic controller configured to set an inactive interval when the stored electric energy reaches a first threshold, the electronic controller inactivating the volatile substance emitter during the inactive interval; and
    the electronic controller configured to set, when the first threshold has not been reached, a first activation frequency or a second activation frequency, the electronic controller configured to activate the volatile substance emitter according to the set activation frequency,
    wherein the electronic controller is configured to set, when the electric energy is being generated at a first speed as measured automatically by the electronic controller, the first activation frequency as the set activation frequency, and the electronic controller is configured to set, when the electric energy is generated at a second speed as measured automatically by the electronic controller, the second activation frequency as the activation frequency,
    wherein the second speed is greater than the first speed, and second frequency is greater than the first frequency.

2. The device according to claim 1, wherein the volatile substance emitter comprises:
    a movable element a movement of which generates an airflow over the at least one volatile substance, said movable element comprising at least one magnet; and
    a magnetic flux generator configured to control movement of the magnet.

3. The device according to claim 1, wherein the emitter comprises an aerosol with a valve storing the at least one volatile substance under pressure.

4. The device according to claim 3, wherein the valve is an electrovalve.

5. The device according to claim 3, wherein the valve is a mechanical valve controlled by a rotary motor.

6. The device according to claim 1, wherein the emitter comprises a piezoelectric mechanism.

7. The according to claim 6, wherein the piezoelectric mechanism is in direct contact with the at least one volatile substance.

8. The according to claim 6, wherein the piezoelectric mechanism is in contact with the at least one volatile substance through a porous wick.

9. The device according to claim 1, wherein the energy being generated is measured at the at least one photovoltaic cell.

10. A method for the automated diffusion of at least one volatile substance, the method comprising:
   periodically diffusing the at least one volatile substance;
   extracting electric energy from at least one battery for diffusing the at least one volatile sub stance;
   storing the electric energy transformed from light energy in the battery; and
   setting emission intervals of the at least one volatile substance by setting automatically by an electronic controller a first activation interval defining time intervals between emitter activations and setting a second activation interval defining time intervals between emitter activations less frequent in time than the emitter activations defined by the first activation interval, the setting of the first and second activation intervals of the emitter depending at least on both the stored electric energy and a speed at which electric energy is being generated as measured automatically by the electronic controller.

11. A non-transitory computer-readable medium product incorporating a program configured, when the program is run on a processor, to control a volatile substance diffusion device to carry out steps comprising:
   periodically diffusing the at least one volatile substance;
   extracting electric energy from at least one battery for diffusing the at least one volatile sub stance;
   storing the electric energy transformed from light energy in the battery; and
   setting emission intervals of the at least one volatile substance by setting a first activation interval defining time intervals between emitter activations and setting a second activation interval defining time intervals between emitter activations less frequent in time than the emitter activations defined by the first activation interval, the setting of the first and second activation intervals of the emitter depending at least on both the stored electric energy and a speed at which electric energy is being generated as measured automatically by the electronic controller.

\* \* \* \* \*